United States Patent
Takahashi et al.

(10) Patent No.: US 7,890,275 B2
(45) Date of Patent: Feb. 15, 2011

(54) PLANAR ELONGATIONAL VISCOSITY MEASURING METHOD AND PLANAR ELONGATIONAL VISCOSITY MEASURING APPARATUS

(75) Inventors: Tsutomu Takahashi, Niigata (JP); Masataka Shirakashi, Niigata (JP); Toshihiro Kawano, Niigata (JP)

(73) Assignee: Nagaoka University of Technology, Nagaoka (JP)

( * ) Notice: Subject to any disclaimer, the term of this patent is extended or adjusted under 35 U.S.C. 154(b) by 344 days.

(21) Appl. No.: 12/161,444

(22) PCT Filed: Dec. 27, 2006

(86) PCT No.: PCT/JP2006/326043

§ 371 (c)(1),
(2), (4) Date: Aug. 12, 2008

(87) PCT Pub. No.: WO2007/099686

PCT Pub. Date: Sep. 7, 2007

(65) Prior Publication Data
US 2010/0228504 A1    Sep. 9, 2010

(30) Foreign Application Priority Data

Feb. 28, 2006   (JP) ............................ 2006-053934

(51) Int. Cl.
*G01N 11/00* (2006.01)
(52) U.S. Cl. ....................................... 702/50; 73/54.01
(58) Field of Classification Search .................. 702/42, 702/50; 73/54.14, 54.31
See application file for complete search history.

(56) References Cited

U.S. PATENT DOCUMENTS 6,220,083 B1 * 4/2001 Collier ...................... 73/54.14

FOREIGN PATENT DOCUMENTS

JP    63-99258 U    6/1988

(Continued)

OTHER PUBLICATIONS

Manabu Kato, et al., Nijigen Taiko Nagare ni Okeru Ryudofuku Kussetsu Sokutei o Mochiita Teijo Heimen Shincho Nendo Sokutei, The Japan Society of Mechanical Engineers 2005 Nendo Nenji Taikai Koen Ronbunshu (2), Sep. 18, 2005, pp. 47-48.

*Primary Examiner*—Bryan Bui
(74) *Attorney, Agent, or Firm*—McDermott Will & Emery LLP

(57) ABSTRACT

A planar elongational viscosity measuring method and apparatus which can advance analysis of planar elongational viscosities for high-viscosity and low-viscosity fluids. As a bomb-shell like bob 2 is pushed into a container 6, a non-Newtonian fluid 9 reaches a planar elongation state in a side space G, counterforce F applied to the bomb-shell like bob 2 at this time is measured, planar elongation stress σ is calculated using the counterforce F and conditions input by a user based on push-up force, the counterforce F, and the horizontal cross-sectional area of the side space G, and the planar elongation stress is divided by a planar elongation speed $\epsilon'$, thereby acquiring a planar elongational viscosity $\eta_{PE}$. Accordingly, it becomes possible to acquire planar elongational viscosities of not only a high-viscosity non-Newtonian fluid, but also a low-viscosity non-Newtonian fluid which is not likely to be solidified, resulting in an advancement of analysis of planar elongational viscosities for high-viscosity and low-viscosity fluids.

8 Claims, 8 Drawing Sheets

FOREIGN PATENT DOCUMENTS

| | | |
|---|---|---|
| JP | 05-072101 | 3/1993 |
| JP | 06-011432 | 1/1994 |
| JP | 06-207898 | 7/1994 |
| JP | 2001-059806 | 3/2001 |

* cited by examiner

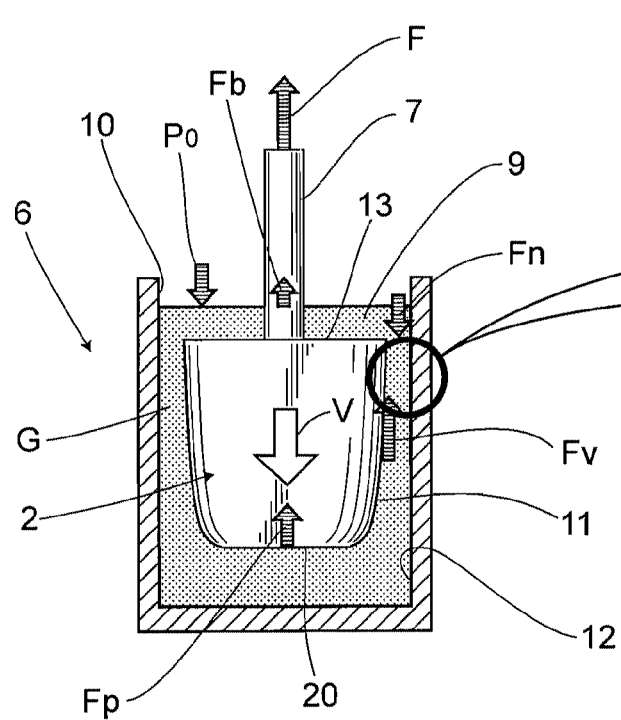
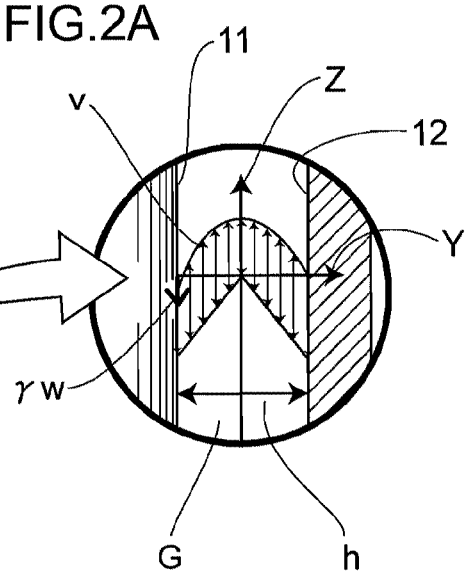
FIG.2
FIG.2A

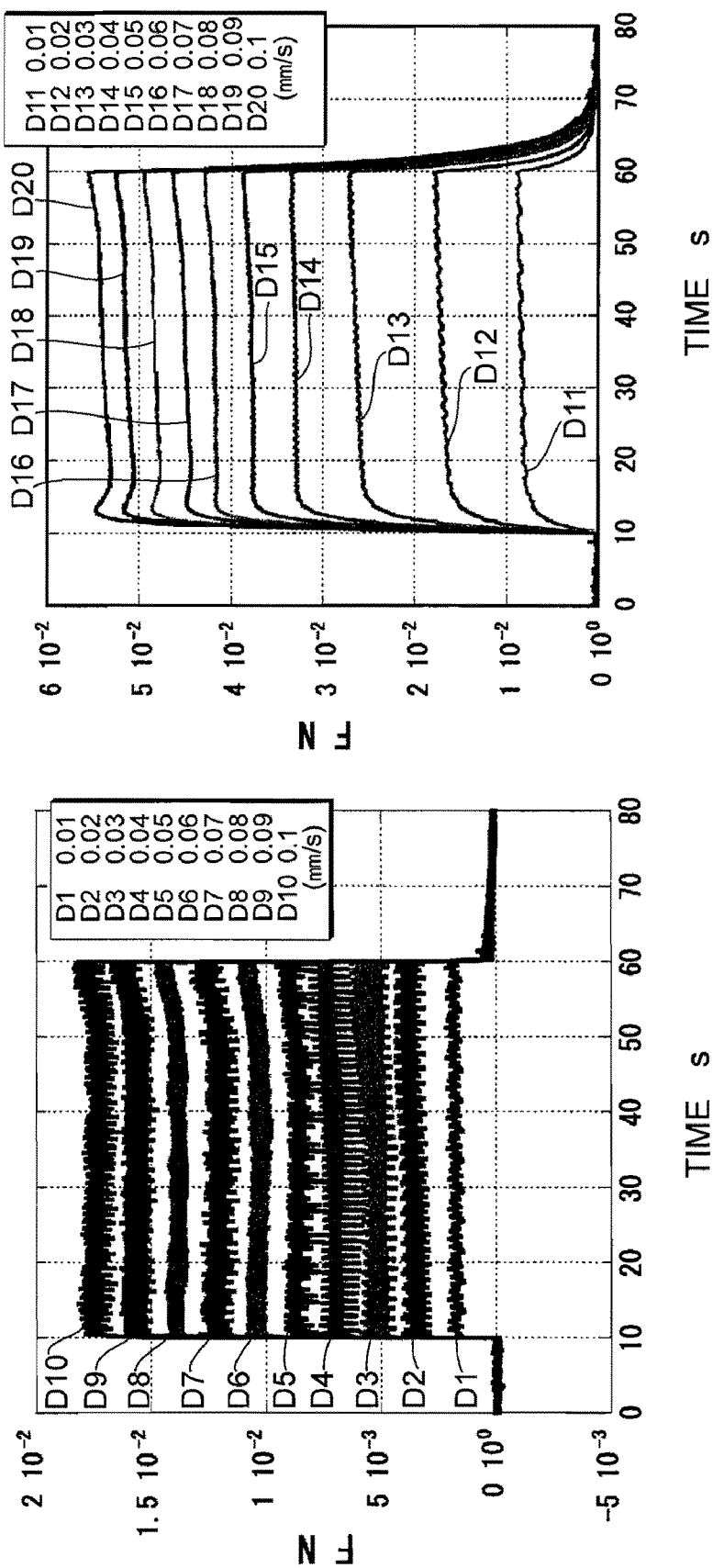

PLANAR ELONGATIONAL VISCOSITY MEASURING METHOD AND PLANAR ELONGATIONAL VISCOSITY MEASURING APPARATUS

CROSS-REFERENCE TO PRIOR APPLICATIONS

This is a U.S. national phase application under 35 U.S.C. §371 of International Patent Application No. PCT/JP2006/326043, filed Dec. 27, 2006, and claims the benefit of Japanese Application No. 2006-053934, filed Feb. 28, 2006, both of which are incorporated by reference herein. The International Application was published in Japanese on Sep. 7, 2007 as International Publication No. WO 2007/099686 A1 under PCT Article 21(2).

FIELD OF THE INVENTION

The present invention relates to a planar elongational viscosity measuring method and a planar elongational viscosity measuring apparatus which are suitable for measuring the planar elongational viscosity of, for example, a non-Newtonian fluid.

BACKGROUND OF THE INVENTION

Conventionally, there is known a rotational viscometer that causes a cylindrical bob (rotor) attached to a rotational axis to be dipped into a fluid to be subjected to a viscosity measurement, rotates the rotational axis, thereby measuring the viscosity of the fluid based on the viscosity resistance applied to the cylindrical bob from the fluid (see, for example, Unexamined Japanese Patent Application Publication No. H6-207898).

SUMMARY OF THE INVENTION

Viscosities of fluids have two kinds: shear viscosities; and elongational viscosities, and elongational viscosities are classified into two kinds: planar elongational viscosities; and uniaxial elongational viscosities. Regarding a Newtonian fluid, such as water or oil, in general, if merely the shear viscosity thereof is measured, the flow thereof can be predicted, but regarding a non-Newtonian fluid, such as a polymer material or a biofluid, the elongational viscosity thereof has an important role, and the planar elongational viscosity becomes an important factor influencing the capacity to form a film or perform blow molding.

In conventional planar elongational viscosity measuring apparatuses which measure a planar elongational viscosity, a solid fluid is used, the one end of the fluid is fixed, the other end of the fluid is elongated by a holder, a planar elongational viscosity arising in the fluid is measured, and analysis of the planar elongational viscosity is advanced using the measurement result. Accordingly, such planar elongational viscosity measuring apparatuses can be used only for a solid and high-viscosity fluid (hereinafter, simply called "high-viscosity fluid"), so that it is difficult to analyze the viscosity of a low-viscosity fluid which is not likely to be formed in a solid (hereinafter, simply called "low-viscosity fluid").

The present invention has been made in view of the foregoing circumstance, and it is an object of the invention to provide a planar elongational viscosity measuring method and a planar elongational viscosity measuring apparatus which can advance analysis of planar elongational viscosities for both high-viscosity fluids and low-viscosity fluids.

A planar elongational viscosity measuring method according to the first aspect of the invention comprises: a measurement step of pushing a bomb-shell like bob having a narrow bottom surface part into a container, in which a fluid subjected to viscosity measurement is filled, from the bottom surface part, and measuring counterforce applied to the bomb-shell like bob from the fluid at this time; a stress calculation step of calculating force that the fluid pushes up the bomb-shell like bob based on an external size of the bomb-shell like bob, and calculating planar elongation stress generated in a space between the bomb-shell like bob and the container based on the calculated push-up force, the counterforce, and a cross-sectional area of the space; and a viscosity calculation step of calculating a planar elongational viscosity by dividing the planar elongation stress by a fluid speed increment rate in the space calculated based on the external size of the bomb-shell like bob and a push-in speed of the bomb-shell like bob into the fluid.

According to the second aspect of the invention, the stress calculation step acquires push-down force originating from planar elongation deformation in the space by subtracting the push-up force from the counterforce, and divides the push-down force by a horizontal area of the space, thereby calculating the planar elongation stress.

According to the third aspect of the invention, the stress calculation step calculates the push-up force by summing: increased buoyancy originating from pushing the bomb-shell like bob into the fluid; bottom-surface push-up drag applied to the bottom surface part of the bomb-shell like bob; and viscosity resistance applied to the bomb-shell like bob in the space.

A planar elongational viscosity measuring apparatus according to the fourth aspect of the invention comprises: pushing means for pushing a bomb-shell like bob having a narrow bottom surface part into a container, in which a fluid to be subjected to viscosity measurement is filled, from the bottom surface part; measurement means for measuring counterforce applied to the bomb-shell like bob from the fluid when the bomb-shell like bob is pushed into the fluid; stress calculation means for calculating force that the fluid pushes up the bomb-shell like bob based on an external size of the bomb-shell like bob, and calculating planar elongation stress generated in a space between the bomb-shell like bob and the container based on the calculated push-up force, the counterforce, and a cross-sectional area of the space; and viscosity calculation means for calculating a planar elongational viscosity by dividing the planar elongation stress by a fluid speed increment rate in the space calculated based on the external size of the bomb-shell like bob and a push-in speed of the bomb-shell like bob into the fluid.

According to the fifth aspect of the invention, the stress calculation means acquires push-down force originating from planar elongation deformation in the space by subtracting the push-up force from the counterforce, and dividing the push-down force by a horizontal area of the space, thereby calculating the planar elongation stress.

According to the sixth aspect of the invention, the stress calculation means calculates the push-up force by summing: increased buoyancy originating from pushing the bomb-shell like bob into the fluid; bottom-surface push-up drag applied to the bottom surface part of the bomb-shell like bob; and viscosity resistance applied to the bomb-shell like bob in the space.

According to the first and fourth aspects of the invention, it is possible to acquire planar elongational viscosities of not only a high-viscosity fluid, but also a low-viscosity fluid which is not likely to be solidified, thereby advancing analysis of planar elongational viscosities for fluids having various viscosities.

According to the second and fifth aspects of the invention, it is possible to acquire planar elongational viscosities of not only a high-viscosity fluid, but also a low-viscosity fluid which is not likely to be solidified, using counterforce, push-up force, and a horizontal area of a space.

According to the third and sixth aspects of the invention, it is possible to calculate push-up forces of not only a high-viscosity fluid but also a low-viscosity fluid which is not likely to be solidified, using increased buoyancy, bottom-surface push-up drag, and viscosity resistance.

BRIEF DESCRIPTION OF THE DRAWINGS

FIG. 2 and FIG. 2A are vertical cross-sectional views showing how drag force works when a bomb-shell like bob is pushed into a container;

FIG. 6 is a timing chart indicating a timing at which the bomb-shell like bob is pushed in;

FIG. 7A and FIG. 7B are perspective views showing a first monitor display example of an analytical result;

DETAILED DESCRIPTION OF THE INVENTION

The preferred embodiment of the invention will be explained below with reference to the accompanying drawings.

(1) Outline of Planar Elongational Viscosity Measurement

Figure 1:
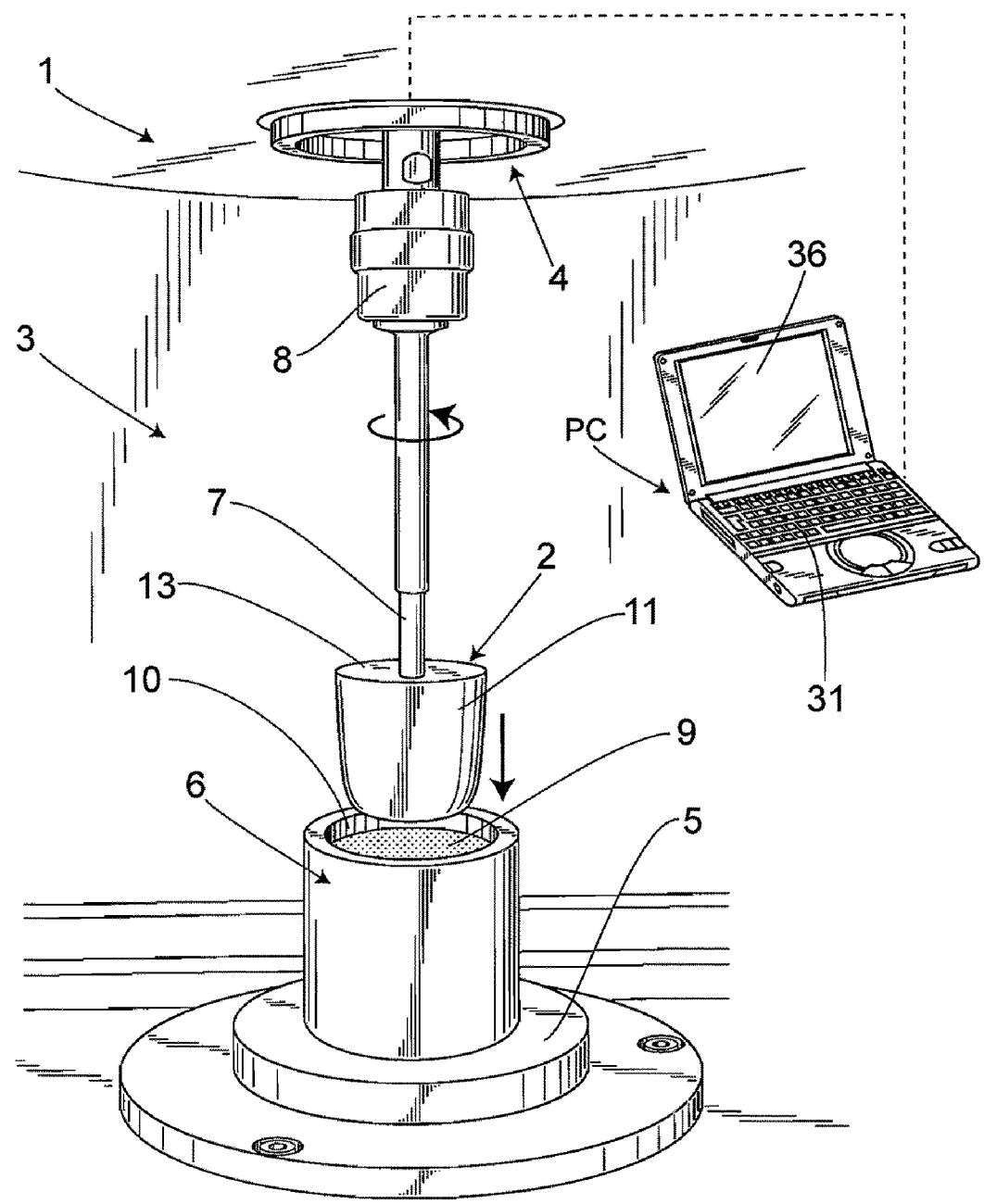
FIG. 1 is a perspective view showing the general structure of a planar elongational viscosity measuring apparatus according to the invention.

In FIG. 1, reference numeral 1 denotes a planar elongational viscosity measuring apparatus which carries out the planar elongational viscosity measuring method of the invention. The planar elongational viscosity measuring apparatus has a structure that a bomb-shell like bob 2, which is completely different from conventional cylindrical bobs, is attached to a rotational viscometer, and a planar elongational viscosity measuring process program for calculating the planar elongational viscosity of a fluid is loaded in a personal computer PC.

In practice, the rotational viscometer (hereinafter called "planar elongation viscometer") to which the bomb-shell like bob 2 is attached comprises an ascending/descending driving unit 4 as push-in means, a base table 5, and a container 6 disposed on the base table 5. The ascending/descending driving unit 4 has a bar-like bob supporting member 7, and moves the bob supporting member 7 up and down along the vertical direction. The bob supporting member 7 has the bomb-shell like bob 2 detachably attached to the leading end thereof, and a load cell 8 as measurement means between the bomb-shell like bob 2 and the ascending/descending driving unit 4.

The planar elongational viscosity measuring apparatus 1 is structured in such a way that, for example, a non-Newtonian fluid 9 as a viscosity measurement target is put in a receiving part 10 of the container 6. In practice, in a case where the planar elongational viscosity of the non-Newtonian fluid 9 is measured, first, the ascending/descending driving unit 4 slides the bob supporting member 7 downwardly for a certain time, thereby causing the bomb-shell like bob 2 to be dipped in the non-Newtonian fluid 9 and brought to temporary a halt. Thereafter, the planar elongational viscosity measuring apparatus 1 slides the bob supporting member 7 at a predetermined push-in speed V, thereby further pushing the bomb-shell like bob 2 into the non-Newtonian fluid 9.

At this time, in the planar elongational viscosity measuring apparatus 1, viscosity resistance applied to the bomb-shell like bob 2 from the non-Newtonian fluid is directly applied to the load cell 8 as counterforce. Accordingly, the planar elongational viscosity measuring apparatus 1 measures the counterforce through the load cell 8, and the load cell 8 transmits the measurement result to the personal computer PC.

The personal computer PC executes a computing process using the measurement result on the basis of a predetermined equation to be discussed later, thereby calculating the planar elongational viscosity of the non-Newtonian fluid 9.

That is, according to the planar elongational viscosity measuring method of the invention, as shown in FIG. 2, as the bomb-shell like bob 2 is pushed into the receiving part 10 of the container 6, the non-Newtonian fluid 9 in the receiving part 10 passes through a side space G between a side wall part 11 of the bomb-shell like bob 2 and an internal wall 12 of the container 10, and pushed out to a top surface part 13 of the bomb-shell like bob 2.

Here, because a distance h between the side wall part 11 of the bomb-shell like bob 2 and the internal wall 12 of the container 10 is narrow in component to the diameter of the container 10, so it is possible to presume that the flow of the non-Newtonian fluid 9 passing through the distance h and going toward the top surface part 13 of the bomb-shell like bob 2 is a two-dimensional flow.

In this case, at the side space G, a velocity distribution v similar to a two-dimensional Poiseulle flow is achieved as shown in FIG. 2A, but in practice, the velocity distribution becomes anti-symmetrical because the bomb-shell like bob 2 moves downwardly. Note that in FIG. 2A, the direction of the flow is indicated by a Z-axis, and the width direction between the side wall part 11 of the bomb-shell like bob 2 and the internal wall 12 of the container 10 (i.e., between two planes) is indicated by a Y-axis, and a side shear rate at the side wall part 11 of the bomb-shell like bob 2 is represented by a symbol $\gamma_w$.

In addition, because the bomb-shell like bob 2 has the distance h to the internal wall 12 of the container 10 which becomes narrower gradually, as the bomb-shell like bob is pushed in the non-Newtonian fluid 9, the non-Newtonian fluid 9 flows within the side space G at a predetermined acceleration. Accordingly, the non-Newtonian fluid 9 reaches a planar elongation flow state.

Meanwhile, six of a flow-in loss, viscosity resistance Fv when the non-Newtonian fluid 9 passes through the side space G, a flow-out loss, push-up force Fp originating from a pressure increment of a bottom surface part 20 of the bomb-shell like bob 2 (hereinafter called bottom-surface push-up force), drag Fb by what corresponds to a buoyant increment originating from a volume increment under a fluid aqueous surface (hereinafter simply called increased buoyancy), and push-down force Fn originating from normal stress generated by a planar elongation flow act on counter force F in the vertical direction generated by pushing the bomb-shell like bob 2 into the non-Newtonian fluid 9. Note that a symbol Po in FIG. 2 is atmospheric pressure.

The flow-in loss and the flow-out loss can be ignored because the flow rates thereof are small in comparison with the viscosity resistance Fv and the bottom-surface push-up drag Fp. Accordingly, four of the viscosity resistance Fv, the bottom-surface push-up drag Fp, the increased buoyancy Fb and the push-down force Fn act on the counterforce F generated by pushing the bomb-shell like bob 2 into the non-Newtonian fluid 9.

Push-up force applied to the bomb-shell like bob 2 (hereinafter called push-up force) is a sum of the increased buoyancy Fb, the bottom-surface push-up drag Fp, and the viscosity resistance Fv, so that a relationship between the push-down force Fn and the counterforce F measured through the load cell 8 can be represented by the following equation.

[Equation 1]

$$Fn = F - Fv - Fp - Fb \quad (1)$$

In practice, in a case where the counterforce F is measured through the load cell 8, the bomb-shell like bob 2 is completely dipped in the non-Newtonian fluid 9 beforehand. Accordingly, there is no difference in buoyancy for the bomb-shell like bob 2 before and after pushing-in. However, because a part of the bob supporting member 7 additionally sinks in the non-Newtonian fluid 9, an increment of buoyancy by what corresponds to the sinking of that part is caused. Moreover, as the bomb-shell like bob 2 is pushed into the non-Newtonian fluid 9, the fluid level of the non-Newtonian fluid 9 rises, resulting in an increment of buoyancy by what corresponds to the rising of the fluid level.

Therefore, buoyancy generated as the bob supporting member 7 sinks in the non-Newtonian fluid 9, and buoyancy originating from the rising of the fluid level due to the bomb-shell like bob 2 being pushed into the non-Newtonian fluid 9 are calculated and summed, thereby acquiring the increased buoyancy Fb.

As the flow field of the non-Newtonian fluid 9 in the side space G is calculated, a pressure loss due to the viscosity is acquired, a pressure increment amount ΔP at the bottom surface part 20 of the bomb-shell like bob 2 based on the pressure gradient is calculated, and the bottom-surface push-up drag Fp is acquired based on the pressure increment amount ΔP.

Further, a flow rate Q is determined to estimate the velocity distribution v at the side space G, so that side shear stress applied to the side wall part 11 of the bomb-shell like bob 2 is estimated, and based on this, the viscosity resistance Fv is acquired.

The push-down force Fn due to the normal stress is acquired using the equation (1), and planar elongation stress σ is acquired using the following equation (2).

Figure 3A:
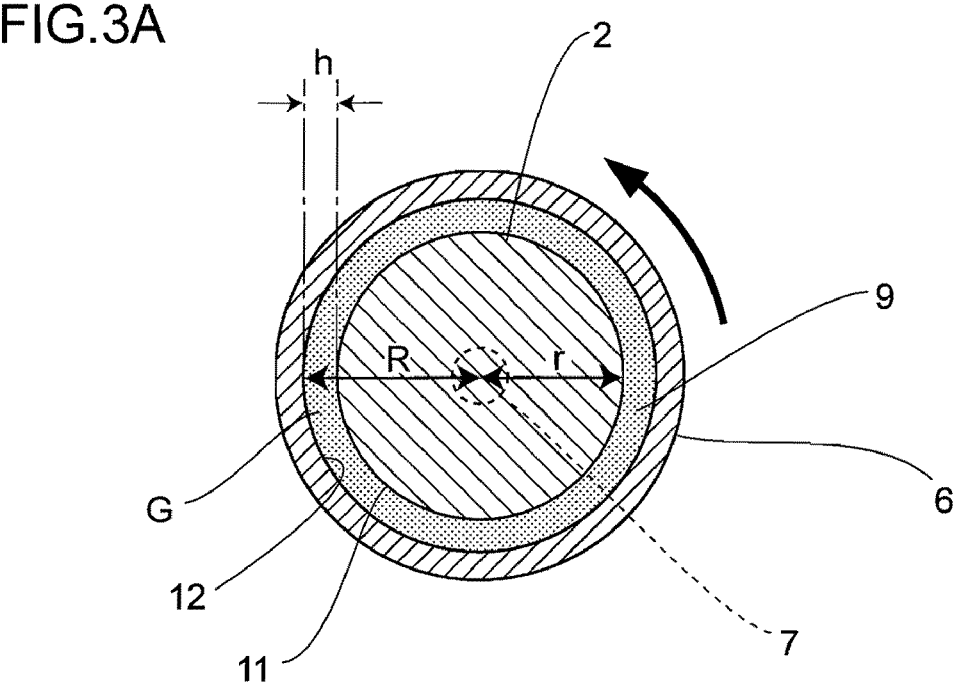
FIG. 3A is a horizontal cross-sectional view and FIG. 3B is a vertical cross-sectional view showing the detailed structure of the bomb-shell like bob and that of the container.
Figure 3B:
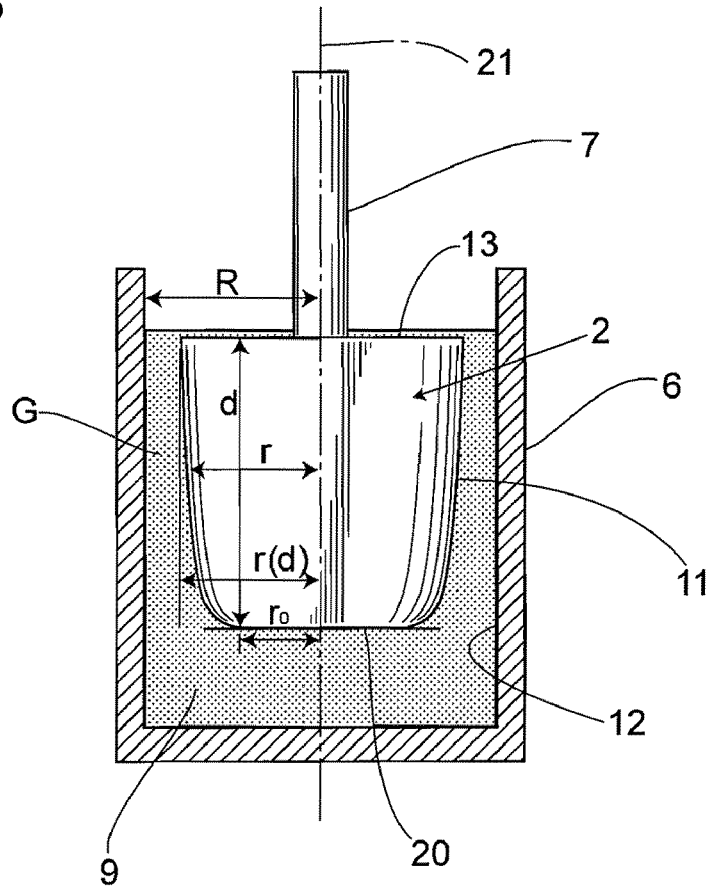
Figure 4:
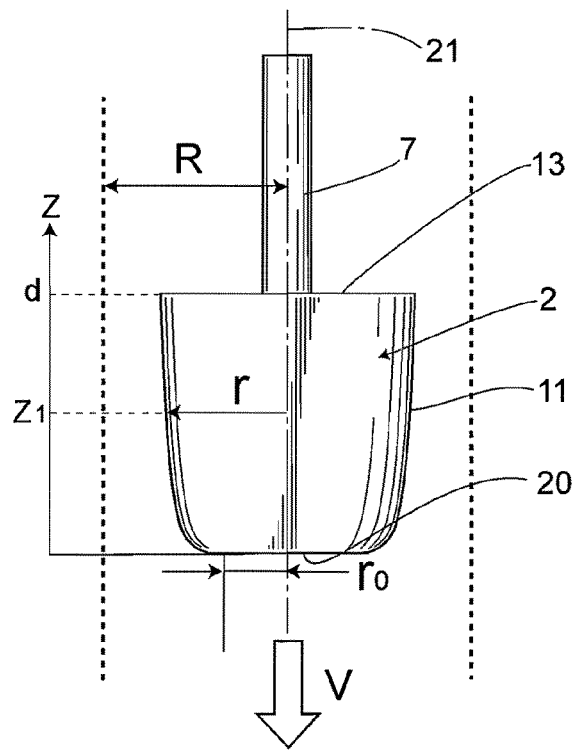
FIG. 4 is a side view showing the detailed structure of the bomb-shell like bob.

[Equation 2]

$$\sigma = Fn/A_{gap} \quad (2)$$

where $A_{gap}$ represents a horizontal cross-sectional area of the side space G as shown in FIG. 3(A) and can be acquired from $\pi R^2 - \pi r^2$. In this case, R is a radius of the receiving part 10 as shown in FIG. 3(B), r is a radius of the bomb-shell like bob 2 at an arbitrary height Z1 in the Z-axis. Note that the Z-axis represents a vertical direction from the bottom surface part 20 of the bomb-shell like bob 2 to the top surface part 13 thereof as shown in FIG. 4 (i.e., the direction of the flow of the non-Newtonian fluid 9), and the arbitrary height Z1 is smaller than the height d of the bomb-shell like bob 2.

In the meantime, the average speed of the non-Newtonian fluid 9 passing through the side space G when the bomb-shell like bob 2 is pushed into the non-Newtonian fluid 9 is accelerated at a certain rate toward the flow direction. A planar elongation speed ε' representing the rate that the flow speed of the non-Newtonian fluid 9 accelerates (i.e., fluid speed increment rate) can be acquired from the following equation (3).

[Equation 3]

$$\varepsilon' = \left\{ \frac{(R^2 - r_0^2)R^2 V}{R^2 - r^2} - R^2 V \right\} \frac{1}{(R^2 - r_0^2)Z1} \quad (3)$$

where $r_0$ is the radius of the bottom surface part 20 of the bomb-shell like bob 2. In this way, the planar elongation speed ε' as the fluid speed increment rate can be determined by the external size of the bomb-shell like bob 2 and the push-in speed V of the bomb-shell like bob 2.

Thus, a planar elongational viscosity $\eta_{PE}$ can be acquired from the following equation (4) by acquiring a ratio between the planar elongation speed ε' and the planar elongation stress σ.

[Equation 4]

$$\eta_{PE} = \sigma/\varepsilon' \quad (4)$$

The push-in speed of the bomb-shell like bob 2 is appropriately changed, thereby enabling an analysis of a relationship between the planar elongation speed ε' and the planar elongational viscosity $\eta_{PE}$.

(2) Planar Elongational Viscosity Measuring Apparatus

As shown in FIG. 1, the planar elongational viscosity measuring apparatus 1 which carries out the planar elongational viscosity measuring method of the invention has a planar elongation viscometer 3 connected to the personal computer PC.

The planar elongation viscometer 3 is structured in such a manner as to measure the counterforce F in the vertical direction applied to the bomb-shell like bob 2 from the non-Newtonian fluid 9 when the bomb-shell like bob 2 is pushed into the receiving part 10 of the container 6, through the load cell 8.

Like conventional viscometers, the planar elongation viscometer 3 can measure resistance in the rotation direction applied to the bomb-shell like bob 2 from the non-Newtonian fluid 9 when the bob supporting member 7 is rotated (see FIG. 3(A)).

In practice, as shown in FIG. 3(B), the container 6 is formed in a cylindrical form having a bottom, and is disposed on the base table 5 in such a way that the central axis of the container matches a central axis 21 of the bomb-shell like bob 2, thereby housing the descending bomb-shell like bob 2 entirely in the receiving part 10.

The receiving part 10 is formed in the same shape as the horizontal cross-sectional shape of the bomb-shell like bob 2, and is set to have the radius R larger than the radius r(d) of the top surface part 13 of the bomb-shell like bob 2, thereby forming the annular side space G between the internal wall 12 and the side wall part 11 of the bomb-shell like bob 2 when the bomb-shell like bob 2 is inserted into the receiving part 10 (see FIG. 3(A)).

Because the side space G is selected so as to be smaller than the radius R of the receiving part 10 and the radius r of the bomb-shell like bob 2, the non-Newtonian fluid flowing in the side space G can be assumed to be a two-dimensional flow.

The bomb-shell like bob 2 is formed of, for example, stainless steel, and is formed in a trapezoidal and conical shape such that the radius r becomes small from the top surface part 13 to the bottom surface part 20, and is formed in a curvature-like shape such that a corner between the bottom surface part 20 and the side wall part 11 is smoothly rounded. The bomb-shell like bob 2 is formed in such a way that the distance h from the internal wall 12 in the receiving part 10 becomes gradually narrow toward the top surface part 13, so that when pushed into the receiving part 10, the bomb-shell like bob causes the non-Newtonian fluid 9 to flow in the side space G at a predetermined acceleration, and causes the non-Newtonian fluid 9 to be in a planar elongation flow state.

In practice, as shown in FIG. 4, the bomb-shell like bob 2 has the radius r which can be expressed by the following equation (5) based on the planar elongation speed $\epsilon'$ of the non-Newtonian fluid and the push-in speed V, and the like.

[Equation 5]

$$r = \sqrt{R^2 - \frac{(R^2 - r_0^2)R^2 V}{\varepsilon'(R^2 - r_0^2)Z1 + R^2 V}} \quad (5)$$

That is, the external diameter size of the bomb-shell like bob 2 can be decided based on the radius R of the receiving part 10 and the push-in speed V of the bomb-shell like bob 2 by the ascending/descending driving unit 4.

According to the embodiment, the bob support member 7 has a non-illustrated thread formed in the leading end thereof, and the bomb-shell like bob 2 is removably threaded with the thread. Accordingly, a user can attach various sizes and forms of bomb-shell like bobs (to be discussed later) to the leading end of the bob support member 7.

Figure 5:
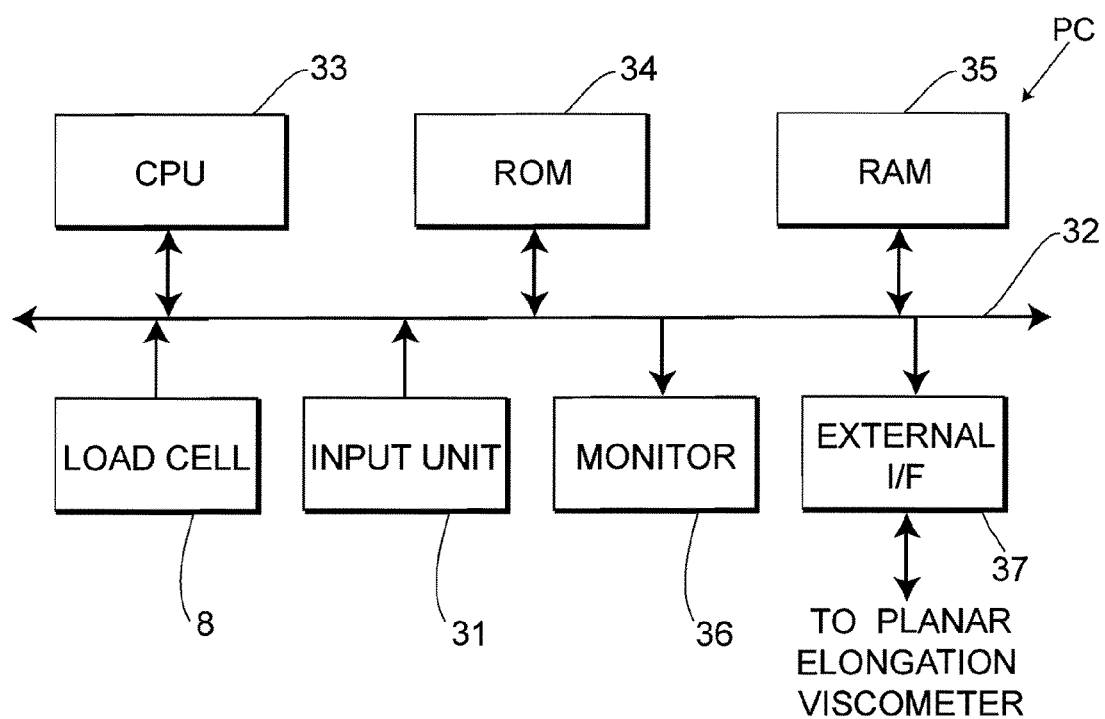
FIG. 5 is a block diagram showing the circuit structure of the planar elongational viscosity measuring apparatus.

As shown in FIG. 5, as the user operates an input unit 31 like a keyboard, various data on a planar elongational viscosity measurement is input to the personal computer PC.

The input unit 31 supplies data input by the user to a CPU 33 through a data bus 32. The CPU 33 which functions as stress calculation means and viscosity calculation means executes planar elongational viscosity measurement in accordance with a planar elongational viscosity-measurement process program stored in a ROM (Read Only Memory) 34, and executes planar elongational viscosity measurement using data input through the input unit 31 and the stress data acquired from the load cell 8 through an external interface 37. At this time, the CPU 33 executes planar elongational viscosity measurement while storing data like a computational result in a RAM (Random Access Memory) 35 as required. The CPU 33 displays a result of the measurement executed in this manner on a monitor 36 in various display forms.

As the user operates the input unit 31 to instruct the start of a planar elongational viscosity measurement, the CPU 33 executes a planar elongational viscosity-measurement process in accordance with the planar elongational viscosity-measurement process program. In this case, the CPU 33 transmits a drive signal to the planar elongation viscometer 3 through the external interface 37.

In response to the drive signal, the planar elongation viscometer 3 drives the ascending/descending driving unit 4 to move the bomb-shell like bob 2 downwardly, and as shown in FIG. 3(A), dips the bomb-shell like bob 2 into the non-Newtonian fluid 9 entirely before the load cell 8 starts measurement.

Figure 6:
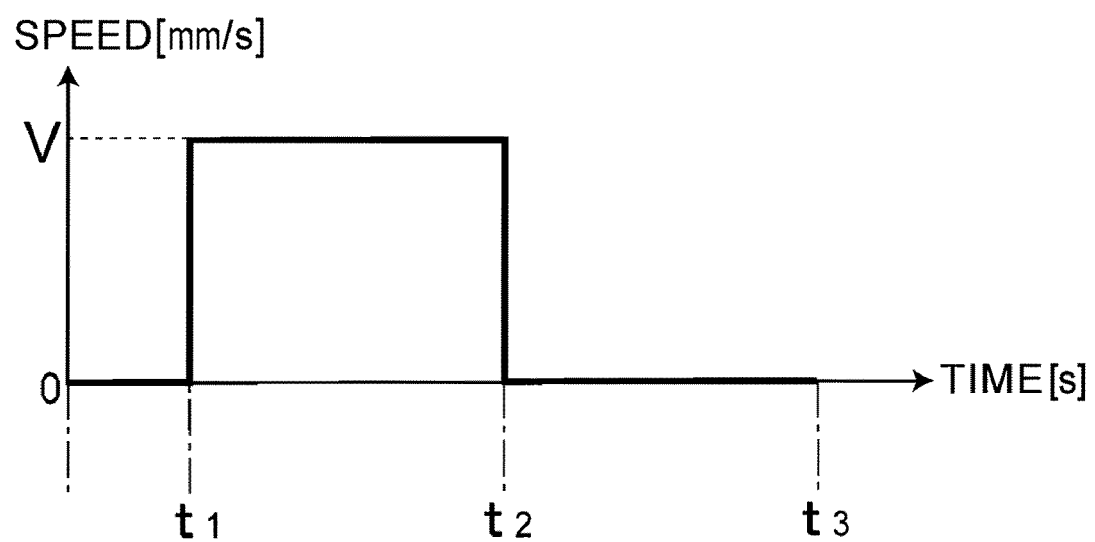

Next, the planar elongation viscometer 3 causes the load cell 8 to start measuring the counterforce F, and as shown in FIG. 6 keeps halting the bomb-shell like bob 2 from the start of the measurement to a predetermined time t1 (e.g., 10 s). Moreover, the planar elongation viscometer 3 drives the ascending/descending driving unit 4 to push the bomb-shell like bob 2 into the non-Newtonian fluid 9 at the push-in speed V during a period after the predetermined time t1 has elapsed and to a predetermined time t2 (e.g., 50 s) (hereinafter, this time interval is called a push-in time $\Delta t1$), and when the predetermined time t2 has elapsed, halts the bomb-shell like bob 2.

In addition, the planar elongation viscometer 3 causes the load cell 8 to measure the counterforce F from the start of the measurement to the predetermined time t2, and causes the load cell 8 to measure the counterforce F during a period after the predetermined time t2 has elapsed and to a predetermined time t3 (e.g., 50 s) and transmits results of those successive measurements as counterforce data to the personal computer PC.

According to the embodiment, because a distance that the bomb-shell like bob 2 can be pushed into the receiving part 10 is, for example, 6 mm and is short, the push-in time $\Delta t1$ is set to about 50 s, and the push-in speed V of the bomb-shell like bob 2 is appropriately set between 0.001 to 0.1 mm/s.

The CPU 33 of the personal computer PC temporarily stores the counterforce data received from the planar elongation viscometer 3 in the RAM 35. In order to calculate the push-down force Fn due to normal stress using the equation (1), the CPU 33 calculates the viscosity resistance Fv, the bottom-surface push-up drag Fp, and the increased buoyancy Fb.

Here, the increased buoyancy Fb is acquired from the following equation (6).

[Equation 6]

$$Fb = \rho \pi R_{shaft}^2 \cdot \left(1 + \frac{R_{shaft}^2}{R^2 - R_{shaft}^2}\right) V t g \quad (6)$$

where $\rho$ represents the density of a fluid subjected to viscosity measurement (in the embodiment, non-Newtonian fluid), $R_{shaft}$ represents the radius of the bob support member 7, and g represents the gravitational acceleration.

Note that the first term (left term) in the bracket of the equation (6) represents buoyancy caused by sinking of the bob support member 7, and the second term (right term) in the bracket of the equation (6) represents buoyancy caused by the rise of the liquid level of the non-Newtonian fluid 9 ejected from the side space G.

Regarding the equation (6), various values, such as the radius $R_{shaft}$ of the bob support member 7 and the fluid density $\rho$, are input by the user through the input unit 31, and the CPU 33 acquires Fb based on the push-in speed V and the push-in time $\Delta t1$.

Moreover, the viscosity resistance Fv can be acquired from the following equation (7).

[Equation 7]

$$Fv = \mu \cdot \gamma w \cdot A_s \quad (7)$$

where $\mu$ represents a shear viscosity coefficient, and is measured beforehand using a conventional rotational viscometer (rotational viscometer). $A_s$ represents the surface area of the side wall part 11 (side wall area) of the bomb-shell like bob 2.

Further, $\gamma_w$ represents a wall shear speed which can be acquired from a velocity distribution v in consideration of the power function at the inlet of the side space G and the outlet thereof for the bomb-shell like bob 2.

The velocity distribution v at the side space G is estimated from a flow rate Q per unit time, and the velocity distribution v is acquired by acquiring a relationship between a shear rate and a viscosity from a normal viscosity measurement and using an equation like a power function. Note that the flow rate Q can be acquired from the following equation (8).

[Equation 8]

$$Q = A_B * v \qquad (8)$$

where $A_B$ represents the bottom surface area of the bottom surface part 20 of the bomb-shell like bob 2 which is acquired from $\pi(ro)^2$.

Furthermore, the surface push-up drag Fp can be acquired from the following equation (9).

[Equation 9]

$$Fp = A_B \cdot \Delta P \qquad (9)$$

where $\Delta P$ represents a pressure rise amount acting on the bomb-shell like bob 2 which can be acquired from an equation representing a pressure gradient.

In this way, the CPU 33 calculates the viscosity resistance Fv, the bottom-surface push-up drag Fp, and the increased buoyancy Fb, and acquires the push-down force Fn from the equation (1) using the counterforce F measured by the load cell 8.

The CPU 33 acquires the planar elongation speed $\epsilon'$ from the equation (3) based on the set push-in speed V or the like, and then acquires the planar elongational viscosity $\eta_{PE}$ from the equation (4) based on the planar elongation speed $\epsilon'$ and the push-down force Fn.

When the counterforce F from the fluid is further measured, the CPU 33 stores the measurement result from the load cell 8 in the RAM 35, and as shown in FIG. 7(B), visibly displays an analysis result according to the push-in speed V (e.g., analysis result D11 when the push-in speed V is 0.01 mm/s) on the monitor 36. Accordingly, the user can figure out the state of the planar elongational viscosity of the non-Newtonian fluid 9 analyzed at this time from the distribution state of waveforms displayed on the monitor 36.

Figure 8A:
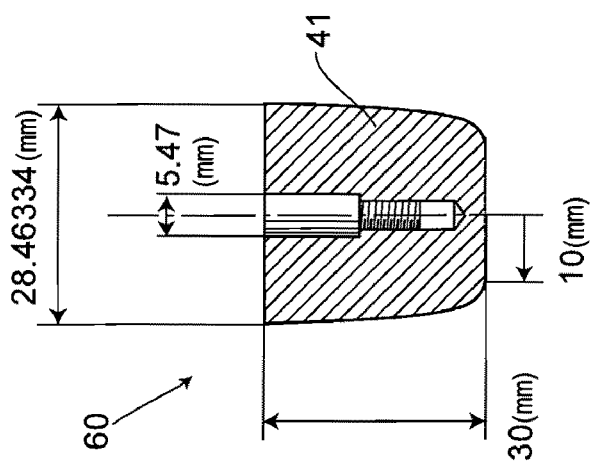
FIG. 8A, FIG. 8B and FIG. 8C are each vertical cross-sectional views showing the side cross-sectional structure of the bomb-shell like bob according to other embodiments of the invention.

Note that the analysis result shown in FIG. 7(B) is one when a bomb-shell like bob 40 shown in FIG. 8(A) is used, and the radius R of the receiving part 10 is 14.46 mm, and the non-Newtonian fluid 9 is the water solution of an interfacial active agent forming a wormlike micelle (CTAB (cetyltrimethylammonium bromide)/NaSal (sodium salicylate)). In this case, as the user operates the input unit 31, various data necessary for measuring a planar elongational viscosity, such as the bottom surface area of the bomb-shell like bob 40, the side wall area thereof, and the push-in speed V, are input into the personal computer PC.

In the foregoing embodiment, the explanation has been given of the case where the low-viscosity non-Newtonian fluid 9 which is not likely to be solidified is used, but the invention is not limited to this case, and can be applied to various low-viscosity fluids like a low-viscosity Newtonian fluid which is not likely to be solidified. FIG. 7(A) shows a result of analyzing a Newtonian fluid (e.g., viscometer calibration standard fluid (JS2000)) using the bomb-shell like bob 40.

In practice, as shown in FIG. 8(A), the bomb-shell like bob 40 comprises a bomb-shell like part 41 formed in a short trapezoidal and conical shape, and a cylinder part 42 both formed integrally. In this case, the bomb-shell like part 41 is formed in such a way that the radius thereof becomes gradually large toward a top surface part 43, so that as the bomb-shell like bob is pushed in the non-Newtonian fluid 9, the non-Newtonian fluid 9 flows at a predetermined acceleration in the side space G with the receiving part 10. Accordingly, the non-Newtonian fluid 9 can be in a planar elongation flow state in the side space G.

In this case, the height of the bomb-shell like part 41 of the bomb-shell like bob 40 is selected to be about 10 mm, the height of the cylinder part is selected to be about 20 mm, the diameter $\Phi$ of the top surface part 43 of the bomb-shell like part 41 is selected to be about 27.67998 mm, and the radius of the bottom surface part is selected to about 10 mm.

The personal computer PC changes the colors of waveforms variously in accordance with a push-out speed V, thereby displaying counterforce F measured at various push-out speeds V on one screen.

Figure 9A:
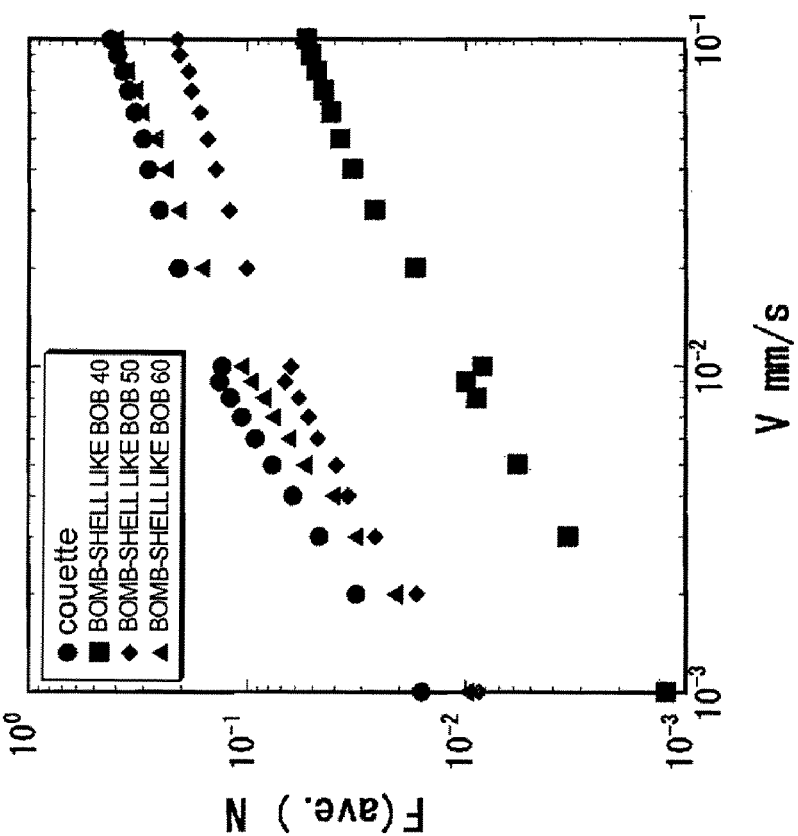
FIG. 9A and FIG. 9B are perspective views showing a second monitor display example of an analytical result.

The personal computer PC calculates average counterforce F (ave) in accordance with a push-in speed V for each Newtonian fluid (JS2000) and non-Newtonian fluid (CTAB) in response to a changeover operation of the input unit 31, and displays the average counterforce F (ave) on one screen as shown in FIG. 9(A).

Figure 8B:
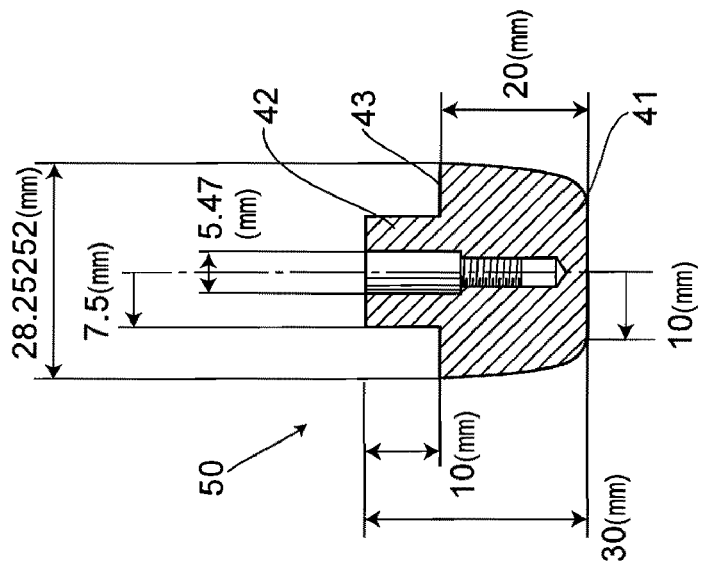
Figure 8C:
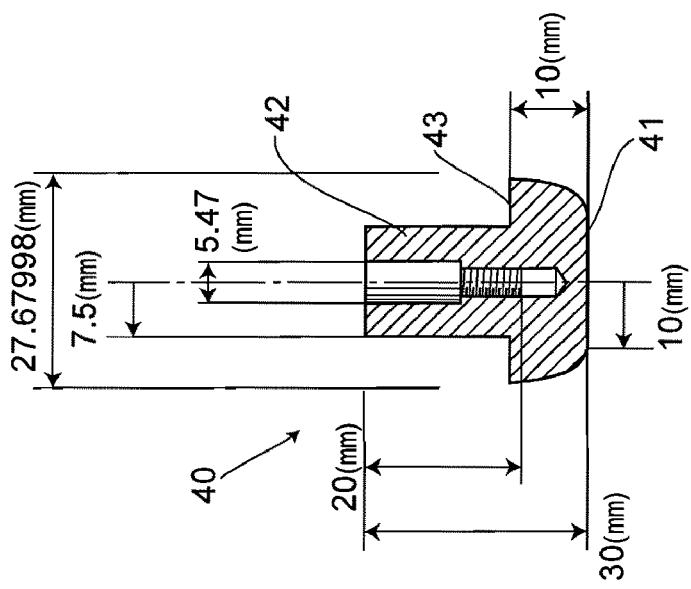
Figure 9B:
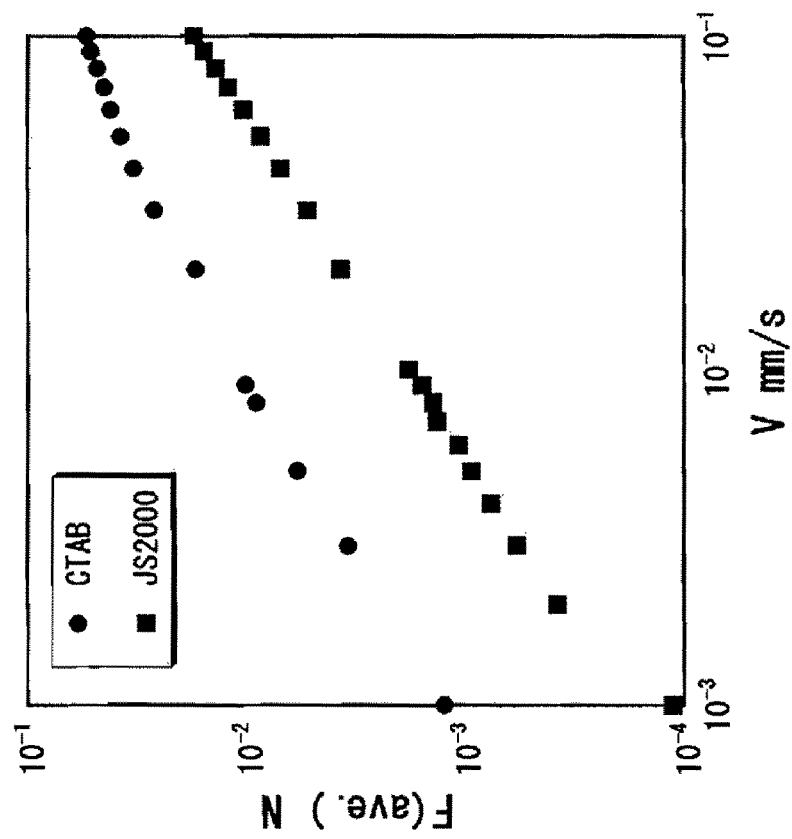

Further, the planar elongational viscosity measuring apparatus 1 can successively attach bomb-shell like bobs 50, 60 shown in FIGS. 8(B) and (C) to the planar elongation viscometer 3, and can display plural measurement results acquired for individual bomb-shell like bobs 50, 60 on one screen of the monitor 36 as shown in FIG. 9(B). Note that FIG. 9(B) shows a measurement result using the foregoing water solution of an interfacial active agent as the non-Newtonian fluid.

(3) Operation and Effectiveness

According to the foregoing structure, the planar elongation viscometer 3 can cause the non-Newtonian fluid 9 to be in a planar elongation state in the side space G by pushing the bomb-shell like bob 2 into the receiving part 10 even if the non-Newtonian fluid has low viscosity and is not likely to be solidified.

In this case, according to the planar elongation viscometer 3, the horizontal cross-sectional shape of the bomb-shell like bob 2 and that of the receiving part 10 are the same, and the bomb-shell like bob 2 is pushed in with the central axis 21 thereof matching the central axis of the container 9, thereby realizing a uniform planar elongation flow in the side space G.

Moreover, according to the planar elongation viscometer 3, counterforce F applied to the bomb-shell like bob 2 at this time is measured, and the measurement result is transmitted to the personal computer PC in real time.

Accordingly, the personal computer PC calculates push-up force (i.e., increased buoyancy Fb, bottom-surface push-up drag Fp and viscosity resistance Fv) applied to the bomb-shell like bob 2 based on the external size of the bomb-shell like bob 2, and calculates planar elongation stress a at the side space G based on the calculated push-up force, the counterforce F, and the horizontal cross-sectional area of the side space G.

Subsequently, the personal computer PC divides the planar elongation stress $\sigma$ by a planar elongation speed $\epsilon'$, which is calculated based on the external size of the bomb-shell like bob 2, and the push-in speed V of the bomb-shell like bob 2 into the non-Newtonian fluid 9, thereby acquiring the planar elongational viscosity $\eta_{PE}$ of the non-Newtonian fluid 9. This facilitates the advance of an analysis of the planar elongational viscosity $\eta_{PE}$ of the non-Newtonian fluid 9 which is not likely to be solidified.

Moreover, the planar elongational viscosity measuring apparatus 1 can measure a planar elongational viscosity which cannot be measured by conventional rotational viscometers by changing a conventionally-used cylindrical bob of the rotational viscometer to the bomb-shell like bob 2, and loading the planar elongational viscosity-measurement process program for executing the foregoing calculation processes like the equations (1) to (4) in the personal computer PC.

As explained above, the invention can directly employ the basic mechanical structures conventionally used, such as an ascending/descending driving unit and a load cell, thereby achieving a manufacturing cost reduction of the planar elongational viscosity measuring apparatus 1.

As explained above, according to the embodiment, the bomb-shell like bob 2 is pushed into the container 6 to cause the non-Newtonian fluid 9 to be in a planar elongation state in the side space G, counterforce F applied to the bomb-shell like bob 2 at this time is measured, and the calculation process is executed in accordance with the equations (1) to (4) using the counterforce F and conditions input by the user, thereby acquiring planar elongational viscosities of not only a high-viscosity non-Newtonian fluid, but also a low-viscosity non-Newtonian fluid which is not likely to be solidified, so that the analysis of planar elongational viscosities for high-viscosity and low-viscosity fluids is advanced.

The present invention is not limited to the foregoing embodiment, and can be changed and modified in various forms. In the foregoing embodiment, the explanation has been given of the case where the planar elongational viscosity measuring apparatus 1 employs a structure that the personal computer PC and the planar elongation viscometer 3 are separate, but the invention is not limited to this case, and can be applied to a planar elongational viscosity measuring apparatus which employs a structure that the personal computer PC and the planar elongation viscometer 3 are combined together.

The invention claimed is:

1. A planar elongational viscosity measuring method comprising:
   a measurement step of pushing a bomb-shell bob having a narrow bottom surface part into a container, in which a fluid to be subjected to viscosity measurement is filled, from the bottom surface part, and measuring counterforce applied to the bomb-shell bob from the fluid at this time;
   a stress calculation step of calculating force that the fluid pushes up the bomb-shell bob based on an external size of the bomb-shell bob, and calculating planar elongation stress generated in a space between the bomb-shell bob and the container based on the calculated push-up force, the counterforce, and a cross-sectional area of the space; and
   a viscosity calculation step of calculating a planar elongational viscosity by dividing the planar elongation stress by a fluid speed increment rate in the space calculated based on the external size of the bomb-shell bob and a push-in speed of the bomb-shell bob into the fluid.

2. The planar elongational viscosity measuring method according to claim 1, wherein the stress calculation step acquires push-down force originating from planar elongation deformation in the space by subtracting the push-up force from the counterforce, and divides the push-down force by a horizontal area of the space, thereby calculating the planar elongation stress.

3. The planar elongational viscosity measuring method according to claim 1, wherein the stress calculation step calculates the push-up force by summing:
   increased buoyancy originating from pushing the bomb-shell bob into the fluid;
   bottom-surface push-up drag applied to the bottom surface part of the bomb-shell bob; and
   viscosity resistance applied to the bomb-shell bob in the space.

4. A planar elongational viscosity measuring apparatus comprising:
   a pushing device pushing a bomb-shell bob having a narrow bottom surface part into a container, in which a fluid to be subjected to viscosity measurement is filled, from the bottom surface part;
   a measurement device measuring counterforce applied to the bomb-shell bob from the fluid when the bomb-shell bob is pushed into the fluid;
   a stress calculation device calculating force that the fluid pushes up the bomb-shell bob based on an external size of the bomb-shell bob, and calculating planar elongation stress generated in a space between the bomb-shell bob and the container based on the calculated push-up force, the counterforce, and a cross-sectional area of the space; and
   a viscosity calculation device calculating a planar elongational viscosity by dividing the planar elongation stress by a fluid speed increment rate in the space calculated based on the external size of the bomb-shell bob and a push-in speed of the bomb-shell bob into the fluid.

5. The planar elongational viscosity measuring apparatus according to claim 4, wherein the stress calculation device acquires push-down force originating from planar elongation deformation in the space by subtracting the push-up force from the counterforce, and divides the push-down force by a horizontal area of the space, thereby calculating the planar elongation stress.

6. The planar elongational viscosity measuring apparatus according to claim 4, wherein the stress calculation device calculates the push-up force by summing:
   increased buoyancy originating from pushing the bomb-shell bob into the fluid;
   bottom-surface push-up drag applied to the bottom surface part of the bomb-shell bob; and
   viscosity resistance applied to the bomb-shell bob in the space.

7. The planar elongational viscosity measuring method according to claim 2, wherein the stress calculation step calculates the push-up force by summing:
   increased buoyancy originating from pushing the bomb-shell bob into the fluid;
   bottom-surface push-up drag applied to the bottom surface part of the bomb-shell bob; and
   viscosity resistance applied to the bomb-shell bob in the space.

8. The planar elongational viscosity measuring apparatus according to claim 5, wherein the stress calculation device calculates the push-up force by summing:
   increased buoyancy originating from pushing the bomb-shell bob into the fluid;
   bottom-surface push-up drag applied to the bottom surface part of the bomb-shell bob; and
   viscosity resistance applied to the bomb-shell bob in the space.

* * * * *